US008831749B2

(12) United States Patent
Boser et al.

(10) Patent No.: US 8,831,749 B2
(45) Date of Patent: Sep. 9, 2014

(54) IMPLANTABLE MEDICAL ELECTRICAL LEAD CONDUCTORS AND CONSTRUCTION METHODS

(71) Applicant: Medtronic, Inc., Minneapolis, MN (US)

(72) Inventors: Gregory A. Boser, Richfield, MN (US); Peter B. McIntyre, Mounds View, MN (US); Kevin R. Seifert, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/664,959

(22) Filed: Oct. 31, 2012

(65) Prior Publication Data

US 2014/0121742 A1    May 1, 2014

(51) Int. Cl.
*A61N 1/05*    (2006.01)
*H01R 43/02*    (2006.01)
*H01R 43/04*    (2006.01)

(52) U.S. Cl.
CPC .............. *A61N 1/0563* (2013.01); *H01R 43/02* (2013.01); *H01R 43/04* (2013.01)
USPC ........................................................ 607/122

(58) Field of Classification Search
USPC ....................................................... 607/116
See application file for complete search history.

(56) References Cited

U.S. PATENT DOCUMENTS

| | | | |
|---|---|---|---|
| 234,962 | A | 11/1880 | Clough |
| 5,115,818 | A | 5/1992 | Holleman et al. |
| 5,728,149 | A | 3/1998 | Laske et al. |
| 5,746,616 | A * | 5/1998 | Mar .............................. 439/245 |
| 5,849,031 | A | 12/1998 | Martinez et al. |
| 6,501,992 | B1 | 12/2002 | Belden et al. |
| 6,544,275 | B1 | 4/2003 | Teoh |
| 6,734,359 | B2 | 5/2004 | Hanazaki et al. |
| 2005/0097737 | A1 | 5/2005 | Webster, Jr. et al. |
| 2010/0133003 | A1 | 6/2010 | Seifert et al. |
| 2010/0137959 | A1 | 6/2010 | Seifert |
| 2011/0079423 | A1 | 4/2011 | Zhao et al. |
| 2011/0282420 | A1 | 11/2011 | Seifert et al. |
| 2012/0130453 | A1 | 5/2012 | Stahmann et al. |

OTHER PUBLICATIONS (PCT/US2013/065095) PCT Notification of Transmittal of the International Search Report and the Written Opinion of the International Searching Authority, Feb. 17, 2014.

* cited by examiner

*Primary Examiner* — Carl H Layno
*Assistant Examiner* — Jon Eric C Morales
(74) *Attorney, Agent, or Firm* — Michael C. Soldner

(57) ABSTRACT

A coiled continuous conductor wire of an implantable medical electrical lead includes a first, electrode length and a second, insulated length, wherein the insulated length of the wire has a radial cross-section defined by a round profile, while the electrode length of the wire has a radial cross-section defined by a flattened profile, a long axis edge of which defines an outer diameter surface of the electrode length. The radial cross-section profile, along the electrode length of wire, is preferably flattened after an entire length of the wire has been coiled.

5 Claims, 6 Drawing Sheets

IMPLANTABLE MEDICAL ELECTRICAL LEAD CONDUCTORS AND CONSTRUCTION METHODS

FIELD OF THE DISCLOSURE

The present invention pertains to implantable medical electrical leads, and, more particularly to conductors and construction methods thereof.

BACKGROUND

Implantable medical systems that are designed to deliver electrical stimulation, for example, to cardiac muscle or the spinal cord, and/or to monitor bodily electrical activity, typically include a relatively compact implantable device to which one or more elongate implantable electrical leads are coupled, for example, like the exemplary system 10 schematically shown in FIG. 1A. FIG. 1A illustrates system 10 including an implantable defibrillator device 500 and a defibrillation lead 100, which is connected to device 500 and extends transvenously therefrom, into a heart of a patient, such that a defibrillation electrode 11 and a pace-sense electrode 13 of lead 100 are located in the right ventricle RV of the heart. Those skilled in the art appreciate that a power source and circuitry of device 500 are contained in a hermetically sealed housing 55 of device 500, which housing 55, being formed from a conductive metal such as titanium, may function as an electrode, in concert with electrode 11, to deliver high voltage pulses for defibrillation therapy in response to a cardiac arrhythmia, for example, sensed by electrodes 13, 11.

FIG. 1A further illustrates device 500 including a connector module 51 that has a port 501 into which a connector terminal 15 of lead 100 is inserted for electrical coupling with the circuitry contained in housing 55, for example, via electrical contacts, which are mounted within port 501 and coupled to the circuitry via hermetically sealed feedthroughs. Suitable constructions for such a connector module and lead connector are known to those skilled in the art. With reference to FIG. 1B, an outer insulation sheath 12 of lead 100 contains a first elongate conductor that couples electrode 11 to a first connector terminal contact 151, and a second elongate conductor that couples electrode 13 to a connector terminal contact pin 153. Typically each of electrodes 11, 13 are joined to the corresponding conductor via a crimp and/or weld joint that may include a separate coupling component. But, to simplify lead construction and/or to streamline a profile of the lead by eliminating at least one joint, it has been proposed that a coiled conductor include an integral electrode length that extends distally out from outer insulation sheath 12 to form electrode 11. Improvements on such a construction are desired, for example, to enhance lead performance in a system such as system 10.

SUMMARY

According to embodiments of the present invention, a continuous conductor wire of an implantable medical electrical lead, which has been formed in a coil, includes a first, electrode length and a second, insulated length, wherein the insulated length of the wire has a radial cross-section defined by a round profile, while the electrode length of the wire has a radial cross-section defined by a flattened profile, a long axis edge of which defines an outer diameter surface of the electrode length. According to some methods of the present invention, the radial cross-section profile of the electrode length of wire is flattened after the wire has been coiled, preferably by rotary swaging. The outer diameter surface of the first, electrode length, by virtue of the flattened profile, has a larger area that faces outward than if the radial cross-section of this same length of wire were left with a round profile.

In some embodiments, a distal end of the coil, in proximity to the electrode length of wire, is formed into a ring-like structure, for example, by welding multiple turns of the distal end of the coil together. A length of the coil corresponding to the first, electrode length of the conductor wire may be between approximately 4 cm and 8 cm, for example, to function as a defibrillation electrode, however, alternate embodiments of the present invention may be directed toward shorter electrode lengths more suitable for sensing only. According to some embodiments, in which the electrode length is appropriate for sensing only, the electrode length includes a shunt portion located in proximity to the insulated length, wherein the shunt portion is overlaid with a relatively thin layer of dielectric material.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals/letters denote like elements, and.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives. Examples of constructions, materials, dimensions and fabrication processes are provided for select elements and all other elements employ that which is known by those skilled in the art.

Figure 1A:
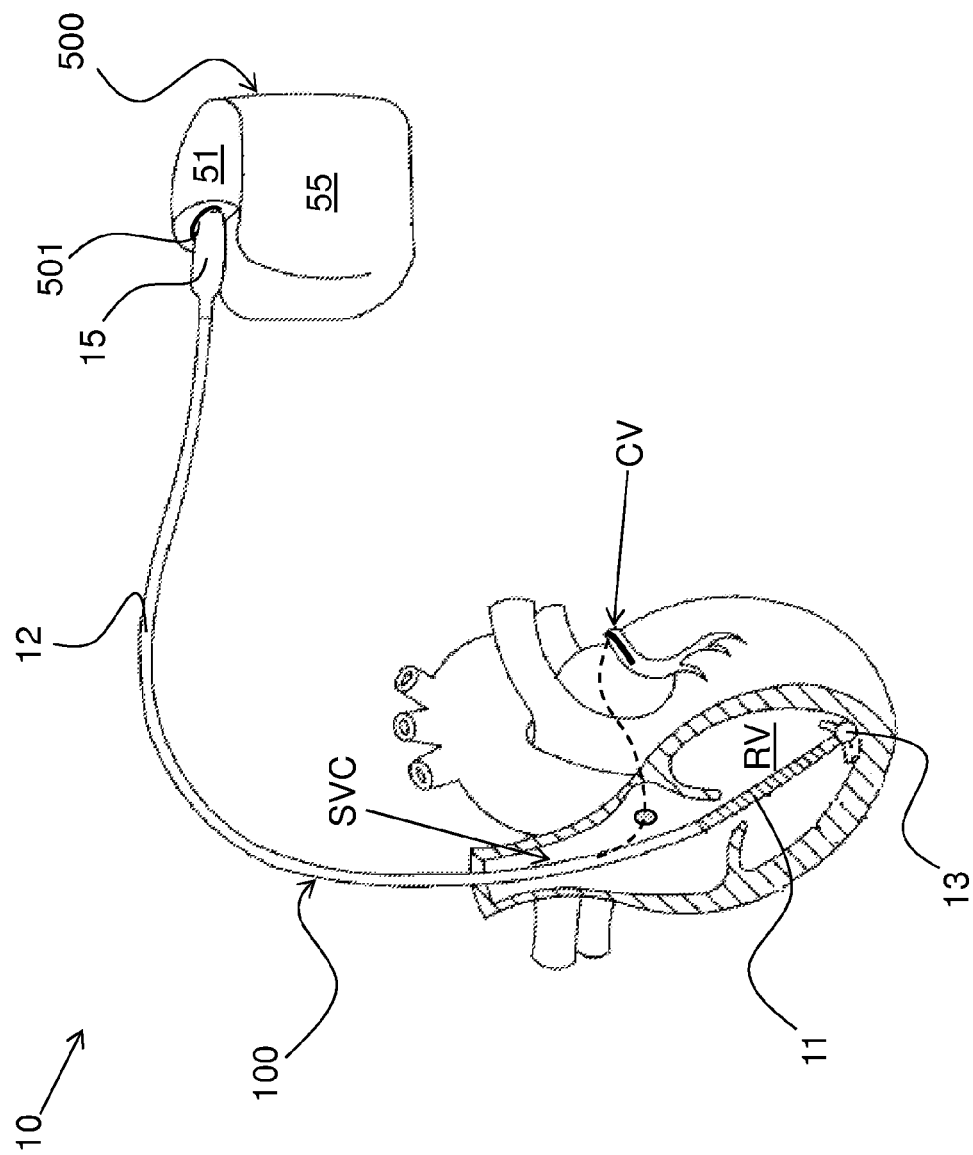
FIG. 1A is a schematic depicting an exemplary implantable medical system.
Figure 1B:
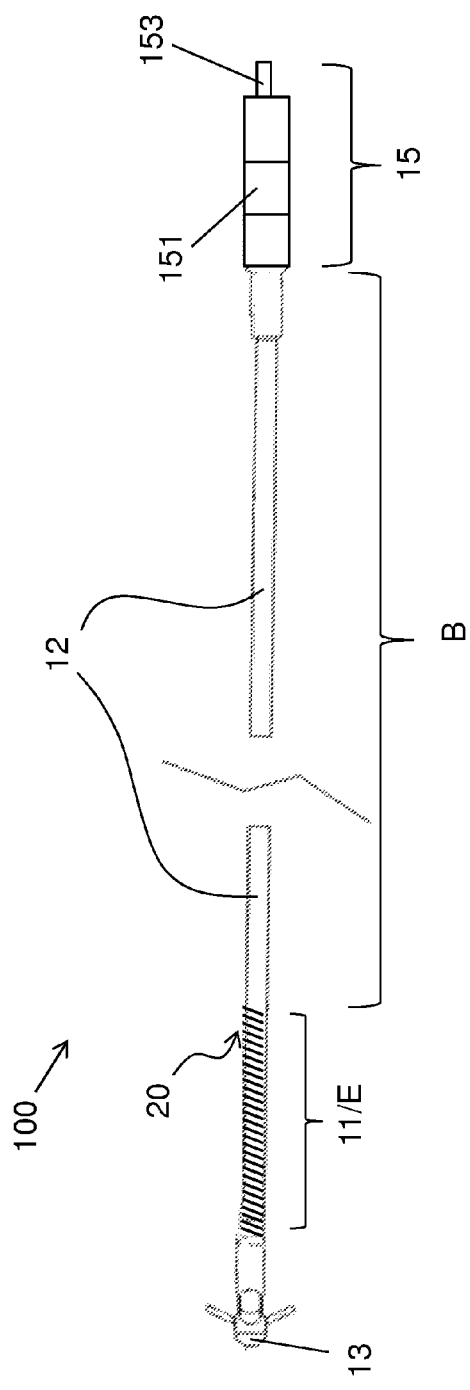
FIG. 1B is a plan view of an implantable medical electrical lead, which may be included in the system of FIG. 1A, and which may be constructed according to some embodiments of the present invention.
Figure 2:
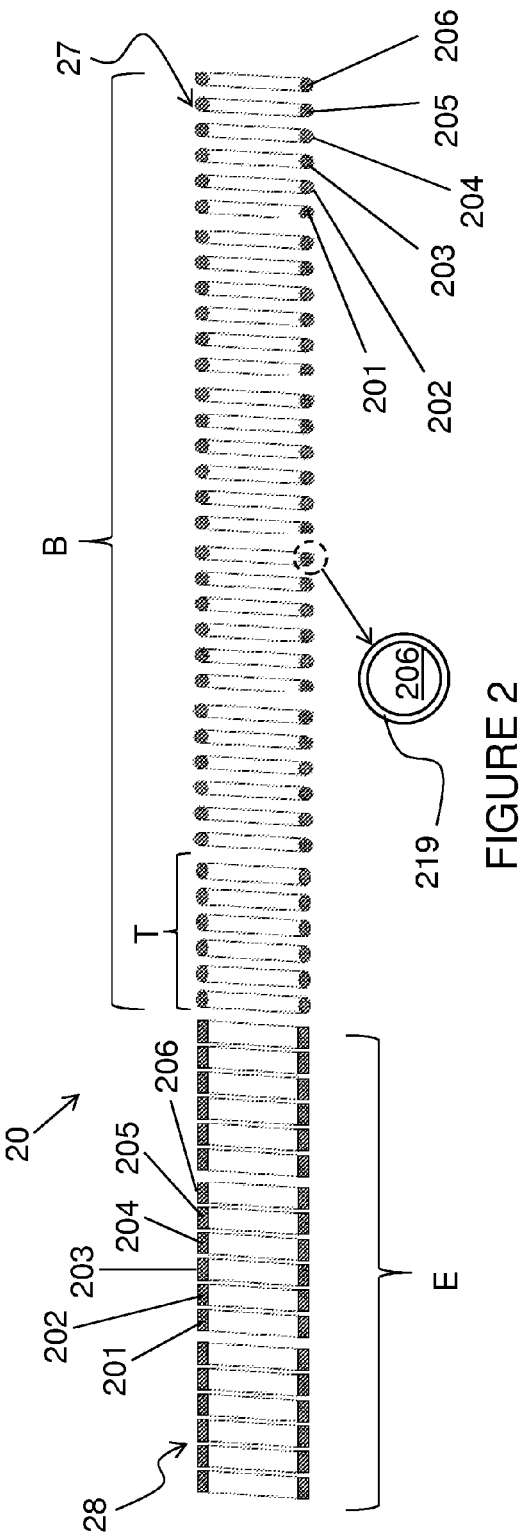
FIG. 2 is a cross-section view, with an enlarged detail view, of a continuous conductor wire coil, according to some embodiments.

FIG. 2 is a cross-section view of a continuous conductor wire coil 20, according to some embodiments, which may be incorporated in lead 100 of FIG. 1B. With reference back to FIG. 1A, it should be noted that embodiments of the present invention include other configurations of leads constructed to locate electrode length E at alternative sites, for example, in the superior vena cava SVC (for defibrillation therapy), or in a coronary vein CV (for pacing therapy). FIG. 2 illustrates coil 20 as a multi-filar coil formed from a plurality of continuous conductor wires 201, 202, 203, 204, 205, 206. The multi-filar construction may be preferred to reduce resistance of coil 20; yet, according to alternate embodiments, coil 20 may be a single-filar coil, for example, including only conductor wire 201 wound in a tighter pitch than illustrated in FIG. 2, or a coil having any other suitable number of filars. Thus, the designation of conductor wire 201-206, as used herein, refers to one or more conductor wires. FIG. 2 illustrates continuous conductor wire 201-206 including a first, electrode length E, and a second, insulated length B, wherein a radial cross-section of insulated length B of conductor wire 201-206 has a round profile 32 (FIG. 3), while a radial cross-section of electrode length E of conductor wire 201-206 has a flattened profile 31, which will be described in greater detail below, in conjunction with FIG. 3. According to preferred methods, the radial cross-section profile of electrode length E of wire 201-206 is flattened after wire 201-206 is wound into coil 20. Conductor wire 201-206 may be formed from any suitable conductive material, such as MP35N alloy, a platinum-iridium alloy (Pt/Ir), tantalum (Ta), a Ta alloy, titanium (Ti), a Ti alloy, or any suitable combination thereof, for example, a Pt/Ir-cladded Ta, or Ta or MP35N having a layer of Pt, titanium-nitride (TiN), or any other suitable coating formed thereover, for example, by sputtering, electro-deposition, ion implantation, or any other suitable coating method. Additional suitable materials for conductor wires 201-206 include cored-composites such as silver-cored MP35N or Ta alloy.

Figure 4:
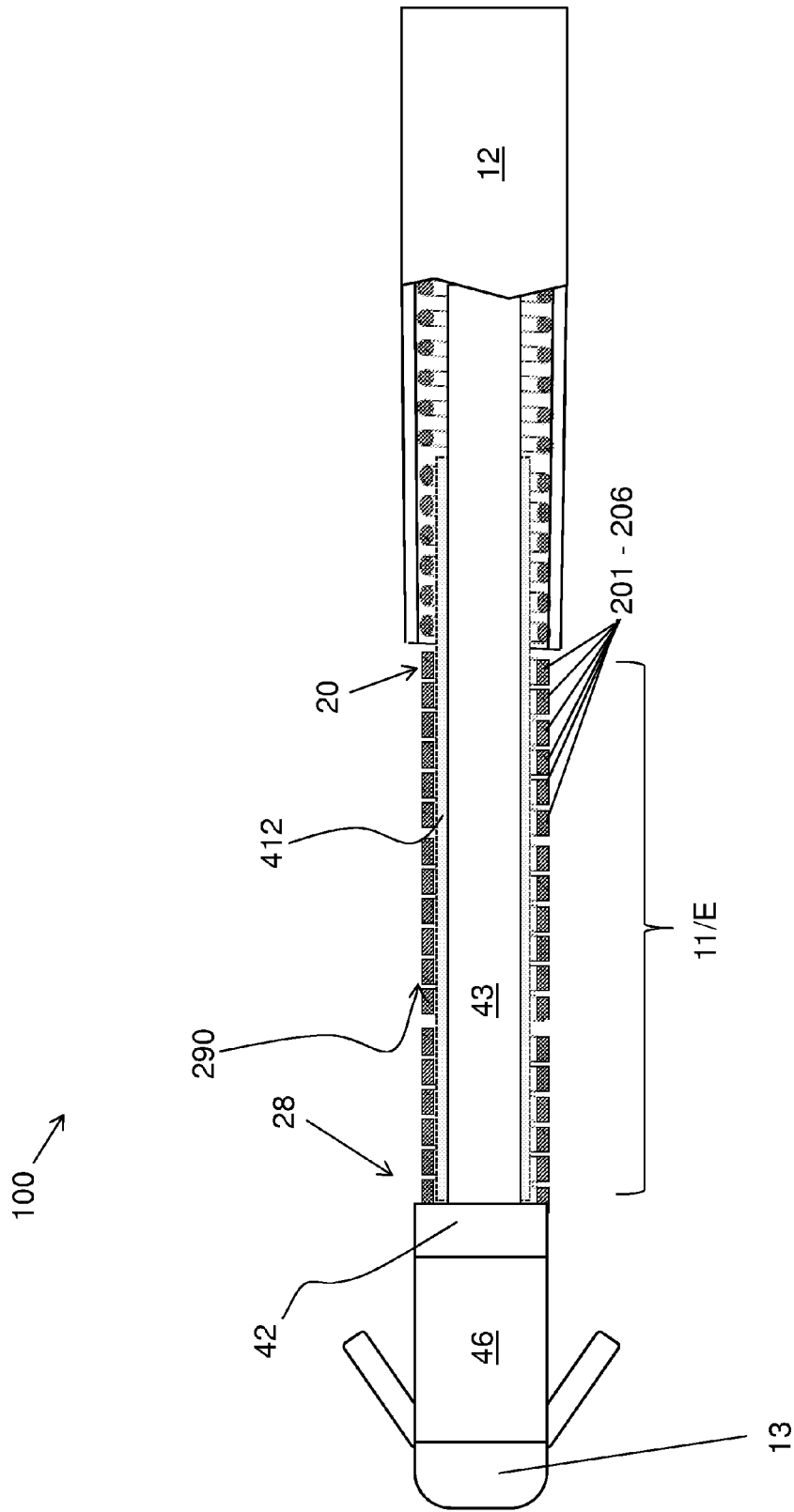
FIG. 4 is an enlarged view, with a cut-away cross-section, of a distal portion of the lead shown in FIG. 1B, according to some embodiments.

With reference to FIGS. 1B and 4, electrode length E of conductor wire 201-206 forms electrode 11, for example, having a length of between approximately 4 cm and 8 cm to function as a defibrillation electrode, while insulated length B of conductor wire 201-206 extends within outer insulation sheath 12, for example, formed from a medical grade silicone rubber or polyurethane. It should be noted that electrode length E may be shorter to function as a pace-sense electrode in alternate embodiments of leads, for example, a lead 600 described below, in conjunction with FIG. 6. The enlarged detail in FIG. 2 shows a radial cross-section of wire 206 along insulated length B, according to some embodiments, wherein an optional jacket of one or more layers of insulation 219, for example, a fluoropolymer and/or a polyimide, encases insulated length B of each conductor wire 201-206. According to some preferred methods, jacket 219 is removed from wire 201-206, along electrode length E, prior to forming the flattened radial cross-section thereof, for example, by laser ablation, or grit blasting, or any other suitable method. With further reference to FIGS. 1B and 2, conductor wire 201-206, at a proximal end 27 of coil 20, is preferably coupled to connector terminal contact 151, and another elongate conductor, for example, an insulated conductor 43 shown in FIG. 4, couples electrode 13 to connector terminal contact pin 153.

Figure 5:
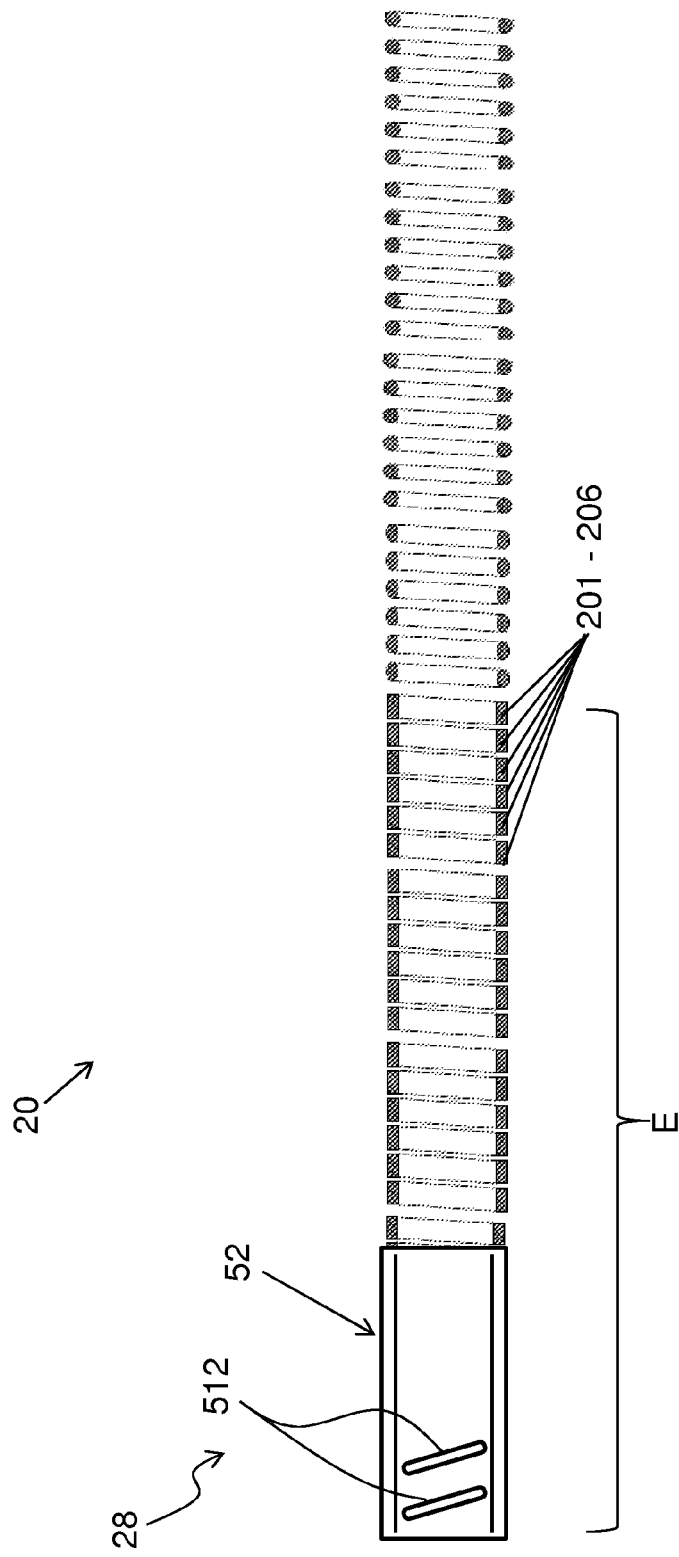
FIG. 5 is a cross-section view of the continuous conductor wire coil including a welded distal end, according to some embodiments.

With further reference to FIGS. 2 and 4, distal end 28 of coil 20 may be terminated with a ring 42 of insulative or conductive material attached thereto, or with a weld, for example, a laser tack weld, or a more substantial laser weld, for example, extending 360 degrees, that welds multiple turns of distal end 28 of coil together to form a ring-like structure, for example, as illustrated in FIG. 5. FIG. 5 is a cross-section view of continuous conductor wire coil 20 including a welded distal end 28 forming a ring 52, according to some embodiments. Ring 52 may be of any suitable length according to the number of filars/turns of coil 20 that are welded together, and, according to the illustrated embodiment, ring 52 may include one or more features, such as slots 512, formed therein, for example, by laser or EDM machining methods known in the art. The one or more features may facilitate the termination of coil 20, for example, by interlocking with mating features of other components of lead 100/600.

FIG. 4 further illustrates a backfill 412, for example, of silicone medical adhesive, that extends between coil 20 and insulated conductor 43, for example to stabilize wire 201-206 along electrode length E and to provide strain relief for coil 20 in proximity to a distal end terminal end of insulation sheath 12. According to some alternate embodiments, rather than including backfill 412, wire 201-206 may be embedded in an outer surface of insulation material that surrounds conductor 43, at least along length E, according to methods known to those skilled in the art.

Figure 3:
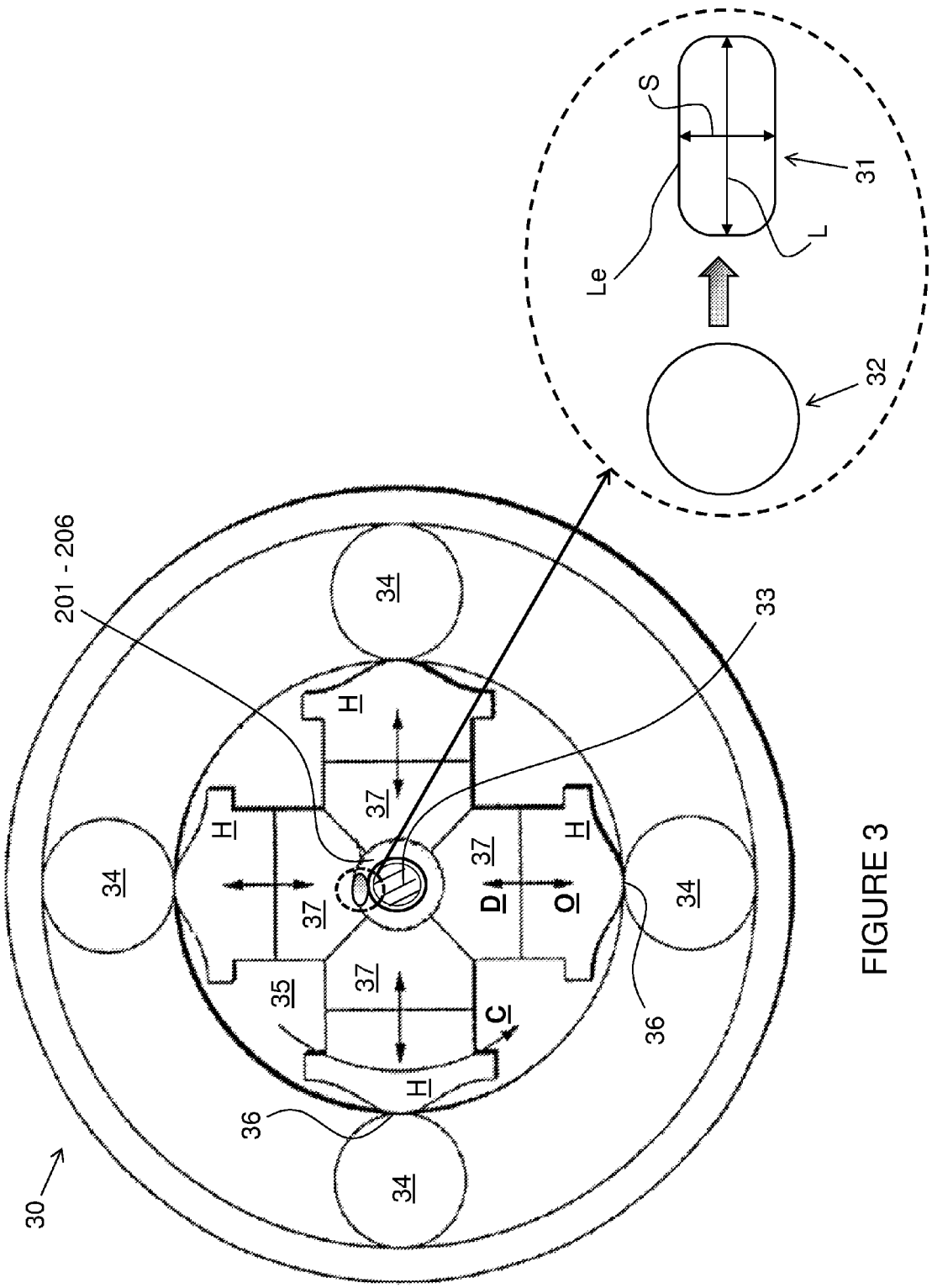
FIG. 3 is a front elevation view of a working portion of an exemplary rotary swaging machine, which may be employed according to some methods of the present invention, along with schematic depicting wire cross-section profiles.

FIG. 3 is a front elevation view of a working portion of an exemplary rotary swaging machine 30, which may be employed according to some methods of the present invention, along with schematic depicting radial cross-section profiles 31, 32 of conductor wire 201-206. FIG. 3 shows conductor wire 201-206, which has been wound in a coil, positioned around a mandrel 33, and mounted within machine 30. FIG. 3 illustrates machine 30 including four dies 37 mounted on a spindle 5 which rotates, per arrow C, so that each die 37 moves, per arrow D, in response to a cam surface 36 of a corresponding hammer H coming into contact with guide rollers 34, and then moves, per arrow O, in response to a centrifugal force created by the spindle rotation, when the corresponding cam surface 36 moves out of contact with rollers 34. It should be noted that only a portion of a length of the coil is positioned within inner peripheral surfaces of dies 37, so that the rest of conductor wire 201-206 that extends along a remainder of the length of the coil is not impacted by dies 37. With reference to the schematic of FIG. 3, as spindle 5 rotates, the 'hammering' of dies 37 plastically deforms, in a radial direction (corresponding to arrows D and O), a radial cross-section of wire 201-206 from an original round profile 32 to flattened profile 31, along a length of the coil that corresponds to a length of each die (into the page), to create first, electrode length E of wire 201-206. It should be noted that rotary swaging is known in the art and may be accomplished with alternative configurations of rotary swaging machines. Alternately, other cold working methods known in the art, for example, performed on a lathe, may be employed to plastically deform the radial cross-section of wire 201-206, for example, from round profile 32 to flattened profile 31. Furthermore, with reference back to FIG. 2, it is contemplated that the cold working method employed to plastically deform the radial cross-section of wire 201-206 into flattened profile 31, along electrode length E, may simultaneously remove the optional insulation jacket 219 from around wire 201-206.

The schematic of FIG. 3 shows flattened profile 31 having a short axis S, a long axis L, and a long axis edge Le, wherein, with reference to FIG. 4, long axis edge Le defines an outer diameter surface 290 of electrode length E. According to an exemplary embodiment, round profile 32 of wire 201-206 has a diameter of approximately 0.005 inch, whereas long axis edge Le of flattened profile 31 extends approximately 0.007 inch, and short axis S approximately 0.003 inch. Thus, by virtue of flattened profile 31, when coil 20 is employed in lead 100, outer diameter surface 290 along electrode length E has a consistently larger area that faces outward from lead 100, than if the radial cross-section of this same length of wire 201-206 had been left with the round profile 32. The larger area of outer diameter surface 290 is useful for increasing defibrillation shock energy delivered by electrode 11, particularly when a smaller diameter of coil 20 is employed to reduce a profile of lead 100.

According to some preferred embodiments, outer diameter surface 290 is made approximately isodiametric with an outer diameter of insulation sheath 12 by slightly enlarging an inner diameter of coil 20 along first electrode length E of wire 201-206, for example, with mandrel 33 (FIG. 3) just prior to swaging. Alternately, coil 20 may be wound such that a distal length thereof, which corresponds to electrode length E of wire 201-206, has a larger diameter than a proximal length thereof, which corresponds to insulated length B. According to the illustrated embodiment of FIG. 4, elongate insulated conductor 43 (i.e. a cabled bundle of MP35N conductor wires contained within a fluoropolymer jacket and/or a silicone or polyurethane sheath) extends within an inner diameter of coil 20 to electrically couple electrode 13 to connector terminal contact pin 153 (FIG. 1B); and an insulator member 46 mechanically joins the assembly of electrode 13 and insulated conductor 43 to coil 20, by any suitable interlocking and/or bonded junction known to those skilled in the art. According to embodiments in which ring 42 is a separate component coupled to distal end of coil 28, ring 42 may have features formed therein (i.e. via EDM or laser machining) to interlock/mate together components, such as coil 20 and insulator member 46. Furthermore, whether or not the diameter of coil 20 is enlarged along electrode length E, prior to flattening, a diameter of distal end 28 of coil 20 may subsequently be reduced, for example, by swaging distal end 28 a second time, around a smaller diameter mandrel than that previously employed, in order fit distal end 28 within ring 42 for a lower profile junction therewith, according to some embodiments.

With reference back to FIG. 2, it should be noted that, according to some methods, coil 20 may be originally wound with two pitches, wherein a pitch over the distal length, corresponding to electrode length E of wire 201-206, is longer than that over the proximal length, corresponding to insulated length B. The longer original pitch of the distal length may be necessary, in some instances, to provide extra longitudinal space between turns of wire 201-206 to accommodate the subsequently flattened profile 31. With further reference back to FIG. 2, a insulated length B of conductor wire 201-206 includes a transition length T at a distal end thereof, in proximity to electrode length E, according to some embodiments, wherein wire 201-206 along transition length T has a profile that is flattened somewhat from round profile 32, but not to the degree of flattened profile 31. This 'intermediate' flattened profile, along transition length T, is also preferably formed after conductor wire 201-206 is wound into coil 20 by a suitable cold working method, for example, rotary swaging.

According to some embodiments, in which conductor wire 201-206 is formed from Ta, Pt, TiN, or other suitable coatings may be applied via sputtering, electro-deposition, ion implantation, or other suitable methods, to form all or a portion of outer diameter surface 290 of electrode length E of wire 201-206; or a Pt-Ir cladding may surround a Ta core to form outer diameter surface 290. Alternately, Ta conductor wire 201-206 includes a native oxide coating, such as tantalum pentoxide ($Ta_2O_5$), or a TiN coating extending over a portion of outer diameter surface 290 of electrode length E, for example, at distal end 28 of coil 20. Any of the Pt, $Ta_2O_5$, and TiN coatings are preferably formed after flattening the cross-section of wire 201-206 along electrode length E. The pentoxide coating may be formed by anodizing and annealing the portion of electrode length E of conductor wire 201-206, for example, by methods known in the art. Likewise the Pt or TiN coating may be formed according to processes known in the art. Any of the Pt, $Ta_2O_5$ and TiN coatings may shift electrical shock energy somewhat proximally during the leading, high amplitude phase (i.e. 600-700 volts) of each biphasic high voltage pulse (delivered through electrode 11, for defibrillation therapy) by attenuating current density at distal end 28. The attenuation of current density at distal end 28 may prevent undesirable current shunting to electrode 13 that could damage cardiac tissue and/or degrade sensing via electrode 13. According to some alternate embodiments, in which conductor wire 201-206 is formed from Pt/Ir or Pt/Ir cladded Ta, ring 42 may be a conductive extension of electrode length E of wire 201-206 to form part of electrode 11, in which case, ring 42 may be formed from Ta having one of the above-described coatings.

Figure 6:
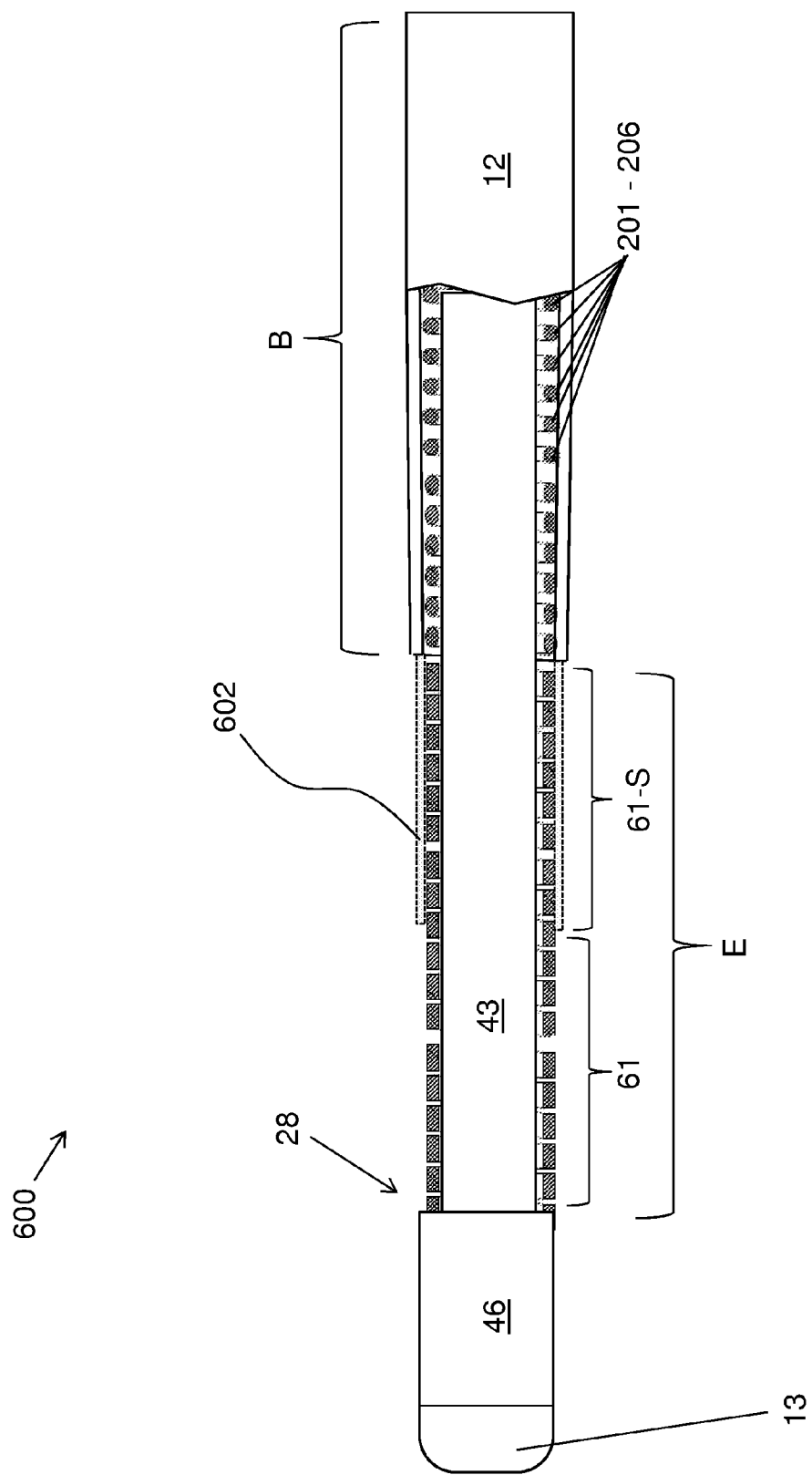
FIG. 6 is a plan view, with a cut-away cross-section, of a distal portion of a pace-sense lead, according to some embodiments.

FIG. 6 is a plan view, with a cut-away cross-section, of a distal portion of pace-sense lead 600, according to some alternate embodiments. With reference back to FIG. 1B, it should be noted that lead 600 may be implanted in coronary vein CV (designated with a dashed line), or in either chamber of the right side of the heart. FIG. 6 illustrates electrode length E of coiled conductor wire 201-206, which has the radial cross-section with flattened profile 31, including an exposed sense portion 61 at distal end 28, and an optional shunt portion 61-S, which extends proximally from sense portion 61. FIG. 6 further illustrates shunt portion 61-S located in proximity to insulated length B and having an outer surface overlaid with a relatively thin layer of dielectric material 602, for example, polyurethane or polyimide. The cross-section profile of wire 201-206 is preferably flattened to form electrode length E, prior to overlaying the outer surface of optional shunt portion 61-S with material 602. Optional shunt portion 61-S can be useful reduce heating of exposed sense portion 61 of electrode length E during magnetic resonance imaging procedures.

In the foregoing detailed description, the invention has been described with reference to specific embodiments. However, it may be appreciated that various modifications and changes can be made without departing from the scope of the invention as set forth in the appended claims.

The invention claimed is:

1. An implantable medical electrical lead comprising a continuous conductor wire wound in a coil, the conductor wire comprising an insulated length, extending distally from a connector terminal of the lead, and an electrode length, extending distally from the insulated length, and wherein the improvement comprises: the insulated length of the wire having a radial cross-section defined by a round profile, while the electrode length of the wire having a radial cross-section defined by a flattened profile, the flattened profile having a long axis and a short axis, and an outer diameter surface of the electrode length being defined by a long axis edge of the flattened profile;

wherein the electrode length of the conductor wire includes a shunt portion located in proximity to the insulated length.

2. A method for constructing an implantable medical electrical lead, the method comprising:

flattening a radial cross-section profile of at least one round conductor wire along a only first length of an overall length of the wire to form an electrode length, the overall length of the at least one wire having been wound in a coil, and the coil extending from a proximal end thereof to a distal end thereof;

insulating a second length of the overall length of the at least one conductor wire; and coupling a connector terminal contact to the proximal end of the coil;

wherein the first length of the at least one conductor wire extends proximally from the distal end of the coil; and
and the second length of the at least one conductor wire extends distally from the coupled connector terminal and toward the first length of the conductor wire; and
wherein flattening the radial cross-section of the at least one wire comprises rotary swaging.

3. A method for constructing an implantable medical electrical lead, the method comprising:
flattening a radial cross-section profile of at least one round conductor wire along a only first length of an overall length of the wire to form an electrode length, the overall length of the at least one wire having been wound in a coil, and the coil extending from a proximal end thereof to a distal end thereof;
insulating a second length of the overall length of the at least one conductor wire; and
coupling a connector terminal contact to the proximal end of the coil;
wherein the first length of the at least one conductor wire extends proximally from the distal end of the coil; and
and the second length of the at least one conductor wire extends distally from the coupled connector terminal and toward the first length of the conductor wire; and
further comprising overlaying a portion of an outer surface of the first length of the conductor wire with a dielectric material, after flattening the radial cross-section profile thereof, the portion being located in proximity to the second length of the conductor wire.

4. A method for constructing an implantable medical electrical lead, the method comprising:
flattening a radial cross-section profile of at least one round conductor wire along a only first length of an overall length of the wire to form an electrode length, the overall length of the at least one wire having been wound in a coil, and the coil extending from a proximal end thereof to a distal end thereof;
insulating a second length of the overall length of the at least one conductor wire; and
coupling a connector terminal contact to the proximal end of the coil;
wherein the first length of the at least one conductor wire extends proximally from the distal end of the coil; and
and the second length of the at least one conductor wire extends distally from the coupled connector terminal and toward the first length of the conductor wire; and
further comprising removing a jacket of one or more layers of insulation from the first length of the at least one conductor wire.

5. A method for constructing an implantable medical electrical lead, the method comprising:
flattening a radial cross-section profile of at least one round conductor wire along a only first length of an overall length of the wire to form an electrode length, the overall length of the at least one wire having been wound in a coil, and the coil extending from a proximal end thereof to a distal end thereof;
insulating a second length of the overall length of the at least one conductor wire; and
coupling a connector terminal contact to the proximal end of the coil;
wherein the first length of the at least one conductor wire extends proximally from the distal end of the coil; and
and the second length of the at least one conductor wire extends distally from the coupled connector terminal and toward the first length of the conductor wire; and
further comprising winding the coil to have a first pitch, over the first length, and a second pitch, over the second length, the first pitch being longer than the second pitch.

* * * * *